(12) United States Patent
Gutknecht et al.

(10) Patent No.: US 6,709,641 B1
(45) Date of Patent: Mar. 23, 2004

(54) METHOD FOR EXTRACTING ANIONS

(75) Inventors: Wilfried Gutknecht, Goslar (DE); Wolfgang Mathy, Langelsheim (DE)

(73) Assignee: H.C. Starck GmbH & Co. KG, Goslar (DE)

( * ) Notice: Subject to any disclaimer, the term of this patent is extended or adjusted under 35 U.S.C. 154(b) by 0 days.

(21) Appl. No.: 09/868,488

(22) PCT Filed: Dec. 14, 1999

(86) PCT No.: PCT/EP99/09914

§ 371 (c)(1),
(2), (4) Date: Jun. 18, 2001

(87) PCT Pub. No.: WO00/39350

PCT Pub. Date: Jul. 6, 2000

(30) Foreign Application Priority Data

Dec. 23, 1998 (DE) .......................... 198 59 683

(51) Int. Cl.[7] .......................... C01G 41/00; C01G 51/00; C01G 33/00; C01G 35/00; C01G 37/00
(52) U.S. Cl. .......................... 423/54; 423/139; 423/63; 423/70; 423/49; 210/684
(58) Field of Search .......................... 423/54, 49, 139, 423/63, 70; 210/684

(56) References Cited

U.S. PATENT DOCUMENTS

| | | | |
|---|---|---|---|
| 3,988,367 A | 10/1976 | Gaudette et al. | 260/534 E |
| 4,010,237 A * | 3/1977 | Harbourne | 423/150.5 |
| 4,055,492 A | 10/1977 | Rupilius et al. | 210/21 |
| 4,230,183 A | 10/1980 | Kalfoglou | 166/274 |
| 5,223,232 A | 6/1993 | Cuillerdier et al. | 423/9 |
| 5,347,071 A * | 9/1994 | Moriya et al. | 588/256 |
| 5,393,431 A | 2/1995 | Campbell et al. | 210/638 |
| 5,795,482 A | 8/1998 | Ehle et al. | 210/634 |

FOREIGN PATENT DOCUMENTS

| | | |
|---|---|---|
| DE | 2648971 | 5/1977 |
| EP | 0 199 905 | 11/1986 |
| EP | 0 267 668 | 5/1988 |
| EP | 0 417 870 | 3/1991 |

OTHER PUBLICATIONS

Erzmetall 51 pp. 110–113 (month unavailable) 1998, Nr. 2. Die Anwendung von Gemischen Anionaktiver und Kationaktiver Sammler in der Flotation, Horst Baldauf, Cornelia Helbig.

Mineral Processing and Extractive Metallurgy Review, (month unavailable) 1995, vol. 15, pp. 153–161, Jan G. H. Du Preez, Diamine and Diammonium Extractants.

* cited by examiner

Primary Examiner—Steven Bos
(74) Attorney, Agent, or Firm—Godfried K. Akurli; Diderico van Eyl

(57) ABSTRACT

The invention relates to a method of extracting anions based on metals of groups IV B to VIII of the periodic table from aqueous solutions thereof, wherein compounds of general formula $$\begin{array}{c} R^1 \\ \diagdown \\ N-(CH_2)_3-N \\ \diagup \\ R^2 \end{array} \begin{array}{c} R^3 \\ \diagup \\ \diagdown \\ R^4 \end{array}$$

Figure 1:
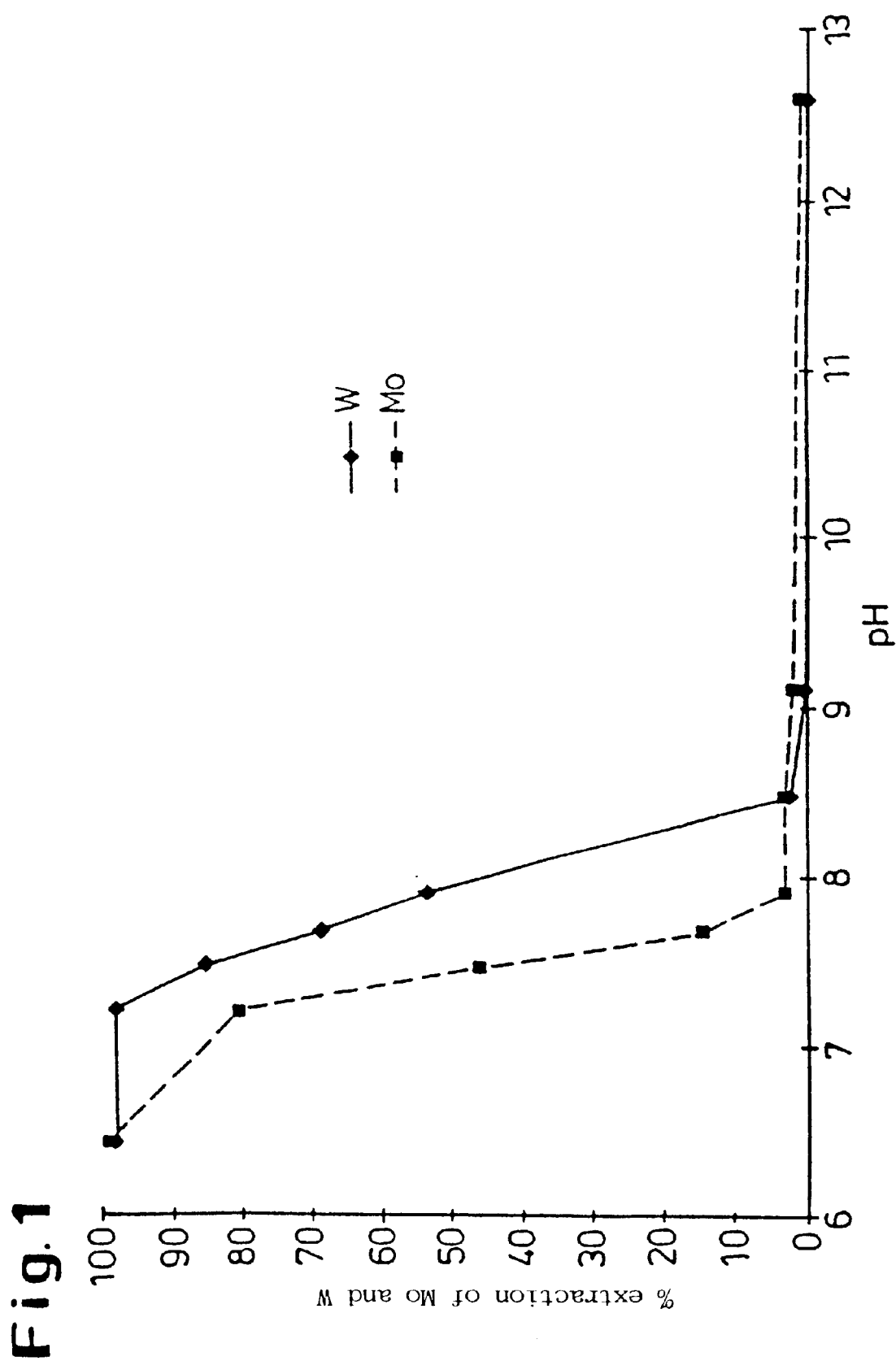

are used as extractants, in which a maximum of two of the $R^1$, $R^2$, $R^3$ and $R^4$ substituents represent hydrogen atoms and the remaining substituents represent identical or different alkyl or aminoakyl groups, which are optionally branched and which contain on average at least 5 C atoms.

7 Claims, 1 Drawing Sheet

METHOD FOR EXTRACTING ANIONS

This application is the National Stage Application of PCT/EP99/09914, which claims a priority from German Applications 198 59 683.9 filed Dec. 23, 1998.

BACKGROUND

The present invention relates to a method of extracting metals of groups V to VII of the periodic table, which exist in the form of anions, metal-containing anions or anionic metal complexes, from aqueous solutions. Extraction from aqueous solutions by means of an organic phase which is insoluble in the aqueous phase and which contains an extractant is a purification step which is widely used during the production of pure metals of groups V to VIII of the periodic table. Extraction methods are firstly used for the separation of impurities which arise from the respective raw materials and which are present in digestion solutions, and secondly are also used for the separation of elements which are adjacent in the periodic table and which cannot be obtained, or which can only be obtained with difficulty, by other methods of separation on account of their chemical affinity. In particular, the separation of pairs of elements comprising W/Mo. Ta/N. Co/Ni and V/Cr is very important industrially. Moreover, extraction is also used as a vehicle for the chemical reaction of sodium tungstate to form ammonium paratungstate, for example. This is achieved by contacting an aqueous solution of sodium tungstate with an organic phase, whereupon the tungstate ions are transferred to the organic phase. and after separating the organic and aqueous phases tungsten cations are stripped from the organic phase with aqueous ammonia solution.

In extractive separation. use is made of the pH- and/or temperature-dependent selective loading capacity and/or of the different loading kinetics of the organic phase with respect to different ions.

Extraction is usually conducted in multi-stage mixer-settler cascades or columns, using counter-current flow.

In addition to the requirement of selectivity of the extractant or of the organic phase with respect to the ions to be separated. the extractant or the organic phase has to have as high a loading capacity as possible at room temperature and must have an approximately neutral pH. Moreover, the extractant should exhibit a solubility in water which is as low as possible, and for process technology reasons the organic phase should not have too high a viscosity.

Known solvent extraction methods only fulfil the aforementioned requirements inadequately, so that there is a desire for improved extraction methods, and particularly for improved extractants. Thus the extraction of cobalt in particular is effected by means of tertiary amines and quarternary ammonium salts, which result in a loading of 10 to 15 g/l cobalt. Higher loadings of 10 to 25 g/l cobalt can be achieved by the use of organophosphoric acids (DEHPA phosphonic acids, phosphinic acids), but there is a risk here of contaminating the cobalt with phosphorus. Moreover, the selectivity in relation to nickel is low. The extraction of molybdenum is mainly carried out by the use of secondary amines as extractants at loadings of 38 to 42 g/l in the organic phase. In the extraction of tungsten with secondary amines, loadings of 60 to 70 g/l W are achieved, whereas tertiary and quarternary amines merely result in a loading of 12 to 15 g/l W.

DE-A 2 530 244 discloses a method of extracting heavy metals by the formation of complexes with amino alkanols. However, amino alkanols of this type have the disadvantage that their solubility in water is too high for industrial use. According to EP-A 505277, iron and zirconium are separated from lanthanide/actinide mixtures by means of propanediamides. The publication by DU PREEZ in Mineral Processing and Extractive Metallurgy Review, 15 (1995) pg. 153 to 161, discloses the use of tetra-substituted diamines for chloro complexes of mono- and divalent metals.

It has now been found that alkyl-substituted 1,3-diaminopropanes are outstandingly suitable for the extraction of anions based on metals of groups V to VIII of the periodic table from aqueous solutions thereof. Moreover, a surprisingly high loading capacity has been found compared with the primary, secondary or tertiary amines and quarternary ammonium compounds which have been customary hitherto.

DESCRIPTION

Accordingly, the present invention relates to a method of extracting anions based on metals of groups IV B to VIII of the periodic table from aqueous solutions thereof which is characterised in that compounds of general formula

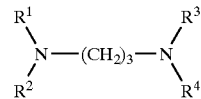

are used as extractants, wherein a maximum of two of the $R^1, R^2, R^3$ and $R^4$ substituents represent hydrogen atoms and the remaining substituents represent identical or different alkyl or aminoalkyl groups. which are optionally branched and which contain on average at least 5 C atoms.

The anions based on metals of the groups IV B to VIII of the periodic table can be the corresponding metal-containing anions (metalates) or anionic metal complexes.

The sum of the C atoms of the R substituents divided by the number of substituents which are not hydrogen atoms should amount to at least 5, so that sufficient insolubility in water is ensured. The average number of C atoms of the R substituents which are not hydrogen atoms should preferably be not more than 10, in order to keep the viscosity of the extractant low, which is advantageous as regards process technology. The preferred extractants according to the invention which correspond to the above formula are characterised in that $R^2$ and $R^4$ are hydrogen atoms. The preferred substituents $R^1$ and $R^3$ are nonyl groups which are optionally branched, most preferably isononyl groups which are optionally branched.

The extractant is preferably used together with an organic solvent which is not soluble in water. Suitable solvents include high-boiling mixtures of hydrocarbons, which may comprise aliphatic. cycloaliphatic and aromatic organic compounds. High-boiling solvent napthas, such as those which can be obtained, for example, from the TOTAL company under the trade name Spirdane® HT, are particularly preferred.

The extractant according to the invention is also preferably used in combination with isodecanol (IDA) as a modifier.

The organic phases which are preferably used according to the invention are those which contain 0.5 to 95% by volume of diaminopropane derivatives, up to 99% by volume of diluent and 0.5 to 20% isodecanol. The organic phases which are most preferably used contain 10 to 20% of a diaminopropane derivative, 5 to 15% isodecanol and 65 to 85% of an organic solvent.

The extraction method according to the invention can be carried out over a temperature range from 15 to 80° C. Temperatures within the range from 20 to 60° C. are preferred.

The aqueous phase can have a pH of 1 to 10, depending on the ions to be extracted.

The method according to the invention is particularly suitable for the extraction of tungsten from solutions which contain molybdenum and tungsten. Solutions of tungsten in caustic soda which result from digestion with caustic soda after the separation of impurities (particularly P, As, Si, Al, Ti, V, Nb, Ta, Sn) by precipitation or ion exchange at pH 8 to 9 can be used directly for extraction. The extractive separation of tungsten and molybdenum is advantageously conducted at a pH of the aqueous phase of 7 to 8.5, most preferably at a pH of 7.3 to 8.2. By comparison: the extraction of tungsten with secondary amines necessitates a pH lower than 6, and a pH of 2 to 3 is required in order to achieve high loadings; extraction with quarternary ammonium compounds necessitates a pH of 7 to 7.5, but tungsten can only be partially stripped with ammonia so that molybdenum/tungsten separation can only be achieved by adding a sulphite. According to the invention, a loading of the organic phase corresponding to about 120 g/l tungsten and less than 2 mg/l Mo is achieved at a pH of about 8. Another advantage of the comparatively high pH of the method according to the invention is that carbon dioxide can advantageously be used as a mineral acid in order to adjust and maintain the pH. In order to recover ammonium paratungstate (APT), the loaded organic phase is stripped with ammonia solution in the manner known in the art after separation of the aqueous phase.

Another method which is preferred according to the invention is the extractive separation of cobalt and nickel from aqueous solutions which contain cobalt and nickel ions. The cobalt and nickel ions are preferably present as chlorides in the aqueous solution. Extraction of cobalt from the aqueous solution necessitates a low pH, i.e. it is conducted in the presence of free hydrochloric acid at a preferred concentration of 150 to 250 g/l of free HCl, so that the cobalt is present as a chloro complex.

The examples below are illustrative example in which all parts and percentages are by weight unless otherwise indicated.

EXAMPLES

The aqueous feed solution and the organic phase (OP) were introduced into a separating funnel, intensively mixed, and separated by allowing the phases to stand.

In the (simulated) two-stage extraction, the OP was twice brought into contact with fresh feed solution. The extraction tests were performed at room temperature (25° C.).

Example 1

| | |
|---|---|
| OP: | 20% N,N-bis-(isononyl)-1,3-diaminopropane |
| | 10% isodecanol |
| | 70% Spirdane HT |
| feed solution: | 90 g/l Co as chloride |
| | 10 g/l Ni as chloride |
| | 200 g/l free HCl |
| quantitative ratio OP: | feed = 1:1 |
| OP loading after 2-stage extraction: | 30.8 g/l Co |
| | 0.15 g/l Ni. |

OP loading after 2-stage extraction:

30.8 g/l Co 0.15g/l Ni.

Example 2

| | |
|---|---|
| OP: | as in Example 1 |
| feed solution: | 91.7 g/l Mo as $Na_2MoO_4$ |
| quantitative ratio OP: | feed = 1:1 |
| pH: | 7.3, adjusted with $H_2SO_4$ |
| OP loading after 2-stage extraction: | 43 g/l Mo. |

Example 3

| | |
|---|---|
| OP: | as in Example 1 |
| feed solution: | 111 g/l W as $Na_2WO_4$ |
| | 60 mg/l Mo |
| quantitative ratio OP: | feed = 1:1 |
| pH: | 7.5, adjusted with $H_2SO_4$ |
| OP loading after 2-stage extraction: | 122 g/l W |
| | <2 mg/l Mo. |

Example 4

| | |
|---|---|
| OP: | as in Example 1 |
| feed solution: | 937 g/l V as $Na_2VO_3$ |
| quantitative ratio feed: | OP = 2:1 |
| pH: | 6.3, adjusted with $H_2SO_4$ |
| OP loading after 1-stage extraction: | 60 g/l V. |

Example 5

| | |
|---|---|
| OP: | as in Example 1 |
| feed solution: | 35 g/l Cr as $Na_2Cr_2O_7$ |
| quantitative ratio feed: | OP = 1:1 |
| pH: | 1.8, adjusted with $H_2SO_4$ |
| OP loading after 1-stage extraction: | 33 g/l Cr. |

Example 6

| | |
|---|---|
| OP: | as in Example 1 |
| feed solution (acidified with HF): | 103 g/l Ta |
| | 62 g/l Nb |
| | 25 g/l Ti |
| quantitative ratio feed: | OP 1:1 |
| OP loading after 1-stage extraction: | 66.6 g/l Ta |
| | 33.1 g/l Nb |
| | 3.8 g/l Ti. |

Example 7

| | |
|---|---|
| OP: | 10% N,N-bis-(isononyl)-1,3-diaminopropane |
| | 10% IDA |
| | 80% Spirdane HT |
| feed: | 60 g/l W as $Na_2WO_4$ |
| | 90 mg/l Mo |
| quantitative ratio feed: | OP = 1:1 |
| pH adjusted with $H_2SO_4$ (variable) | |

| | |
|---|---|
| OP loading after 1-stage extraction: | see FIG. 1. |

FIG. 1 show s the percentages of the metals which were transferred to the OP as a function of pH.

Although the present invention has been described in detail with reference to certain preferred versions thereof, other variations are possible. Therefore, the spirit and scope of the appended claims should not be limited to the description of the versions contained therein.

What is claimed is:

1. A method comprising extracting anions based on metals of groups IV B to VIII of the periodic table from aqueous solutions thereof with an extractant of general formula:

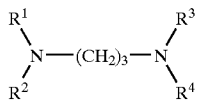

wherein a maximum of two of the $R^1$, $R^2$, $R^3$ and $R^4$ substituents represent hydrogen atoms and the remaining substituents represent identical or different alkyl or aminoalkyl groups, which are optionally branched and wherein the sum of the C atoms of the R substituents divided by the number of substituents which are not hydrogen atoms is at least 5 C atoms.

2. The method according to claim 1, wherein $R^2$ and $R^4$ are hydrogen atoms.

3. The method according to claim 1, wherein $R^1$ and $R^3$ are nonyl groups which are optionally branched.

4. The method according to claim 1, wherein the extractant is used in combination with a diluent.

5. The method according to claim 1, wherein the extractant is used in combination with isodecanol as a modifier.

6. The method according to claim 1, wherein the aqueous solution contains tungsten and molybdenum anions and tungsten anions are extracted at a pH of 7.5 to 8.5.

7. The method according to claim 1, wherein the aqueous solution contains anions which contain cobalt and nickel and cobalt anions are extracted.

* * * * *